United States Patent
Harada et al.

(10) Patent No.: US 9,586,971 B2
(45) Date of Patent: Mar. 7, 2017

(54) GREEN SULFUR BACTERIA VARIANT AND BACTERIOCHLOROPHYLL

(71) Applicant: KURUME UNIVERSITY, Kurume-shi, Fukuoka (JP)

(72) Inventors: Jiro Harada, Kurume (JP); Masato Noguchi, Kurume (JP); Hitoshi Tamiaki, Kusatsu (JP)

(73) Assignee: Kurume University, Kurume (JP)

( * ) Notice: Subject to any disclaimer, the term of this patent is extended or adjusted under 35 U.S.C. 154(b) by 8 days.

(21) Appl. No.: 14/378,096

(22) PCT Filed: Feb. 12, 2013

(86) PCT No.: PCT/JP2013/053295
§ 371 (c)(1),
(2) Date: Aug. 11, 2014

(87) PCT Pub. No.: WO2013/122064
PCT Pub. Date: Aug. 22, 2013

(65) Prior Publication Data
US 2015/0005490 A1   Jan. 1, 2015

(30) Foreign Application Priority Data
Feb. 13, 2012   (JP) .................. 2012-028919

(51) Int. Cl.
| | |
|---|---|
| C12N 9/99 | (2006.01) |
| C07D 487/22 | (2006.01) |
| C12R 1/01 | (2006.01) |
| C12P 17/18 | (2006.01) |
| C12N 9/10 | (2006.01) |

(52) U.S. Cl.
CPC ......... *C07D 487/22* (2013.01); *C12N 9/1007* (2013.01); *C12P 17/182* (2013.01); *C12R 1/01* (2013.01); *Y02P 20/52* (2015.11)

(58) Field of Classification Search
None
See application file for complete search history.

(56) References Cited

PUBLICATIONS

Maresca (Thesis, Penn State University, May 2007, pp. 1-296).*
Vogl et al. (Frontiers in Microbiology, vlo. 3, Aug. 2012, pp. 1-12).*
Chen et al., *Science*, 329: 1318-1319 (2010).
Frigaard et al., *Methods Mol. Biol.*, 274: 325-340 (2004).
Frigaard et al., *Photosynthesis Research*, 78: 93-117 (2003).
Ganapathy et al., *Proc. Natl. Acad. Sci. USA*, 106: 8525-8530 (2009).
Harada et al., *Scientific Reports*, 2: 671 (Sep. 19, 2012).
Orf et al., *Biochimica et Biophysica Acta*, 1827: 493-501 (Jan. 24, 2013).
Prokhorenko et al., *J. Phys. Chem. B*, 106: 5761-5768 (2002).
Risch et al., *Liebigs Annalen der Chemie*, 4: 343-347 (1988).
Sasaki et al., *Bulletin of the Chemical Society of Japan*, 77: 797-800 (2004).
Tamiaki et al., *Bioorganic & Medicinal Chemistry Letters*, 9: 1631-1632 (1999).
Tamiaki, *Coordination Chemistry Reviews*, 148: 183-197 (1996).
Tamiaki et al., *Low Temperature Science*, 67: 339-346 (2009).
Tamiaki et al., *Photosynthesis Research*, 107: 133-138 (2011).
Tamiaki et al., *Tetrahedron*, 59: 4337-4350 (2003).
Vogl et al., *Frontiers in Microbiology*, 3: 288 (Aug. 10, 2012).
Japanese Patent Office, International Search Report in International Patent Application No. PCT/JP2013/053295 (Apr. 23, 2013).
Japanese Patent Office, Written Opinion in International Patent Application No. PCT/JP2013/053295 (Apr. 23, 2013).
Harada et al., *FEBS Letters*, 579: 1983-1987 (2005).
Maresca et al., *Journal of Bacteriology*, 186(9): 2558-2566 (2004).
Miyatake et al., *Journal of Photochemistry and Photobiology C: Photochemistry Reviews*, 6: 89-107 (2005).
Niedzwiedzki et al., *The Journal of Physical Chemistry B*, 118: 2295-2305 (2014).
Oostergetel et al., *FEBS Letters*, 581: 5435-5439 (2007).
Orf et al., *Photosynth. Res.*, 116: 315-331 (2013).
Tokita et al., *Photosynth. Res.*, 108: 183-190 (2011).
Tsukatani et al., *Photochem. Photobiol. Sci.*, 12: 2195-2201 (2013).
European Patent Office, Supplementary European Search Report in European Patent Application No. 13748805.2 (Sep. 16, 2015).

* cited by examiner

*Primary Examiner* — Hope Robinson
(74) *Attorney, Agent, or Firm* — Leydig, Voit & Mayer, Ltd.

(57) ABSTRACT

Provided is a strain permitting genetic engineering of green sulfur bacteria that synthesize bacteriochlorophyll e; isolated green sulfur bacterium *Chlorobaculum limnaeum* strain RK-j-1 with accession number NITE BP-1202; isolated transformed *Chlorobaculum limnaeum* strain obtained by transformation of strain RK-j-1, preferably *Chlorobaculum limnaeum* dbchU strain with accession number NITE BP-1203 wherein bchU gene is disrupted; a production method of bacteriochlorophyll f containing a step of cultivating *Chlorobaculum limnaeum* strain dbchU; and bacteriochlorophyll f obtained by the aforementioned production method.

19 Claims, 3 Drawing Sheets

BChl c: $R_7$ = $CH_3$, $R_{20}$ = $CH_3$
BChl d: $R_7$ = $CH_3$, $R_{20}$ = H
BChl e: $R_7$ = CHO, $R_{20}$ = $CH_3$
BChl f: $R_7$ = CHO, $R_{20}$ = H $3^1$-Configuration = R or S
$X_1, X_2, X_3, X_4$ = H or $CH_3$

GREEN SULFUR BACTERIA VARIANT AND BACTERIOCHLOROPHYLL

CROSS-REFERENCE TO RELATED APPLICATIONS

This patent application is the U.S. national phase of International Patent Application No. PCT/JP2013/053295, filed Feb. 12, 2013, which claims the benefit of Japanese Patent Application No. 2012-028919, filed on Feb. 13, 2012, which are incorporated by reference in their entireties herein.

TECHNICAL FIELD

The present invention relates to a green sulfur bacterium variant and bacteriochlorophyll, and to the field of genetic engineering of green sulfur bacterium.

BACKGROUND ART

Green sulfur bacteria are obligatory anaerobic phototrophs that grow only by photosynthesis. Therefore, they have superior photosynthetic capability, and characteristically contain chlorosome which is an extramembranous antenna system adapted to an extremely weak light. The light-harvesting part in the chlorosome is formed from self-aggregates consisting only of pigments free of the involvement of protein (non-patent document 1). This is the sole exception since pigments perform function in a protein support in the antenna system of all other photosynthetic organisms. Chlorosome can be isolated and purified easily from the living organism, and can be reconstituted after being decomposed outside the living organism. Furthermore, when a pigment that induces a photochemical reaction is added during reconstitution, functional aggregates can be created easily (non-patent document 2).

As self-aggregating pigments in the chlorosome, bacteriochlorophyll (BChl) c, d and e are known (FIG. 1), and which pigment is employed varies depending on the species of the green sulfur bacteria. BChl f and a green sulfur bacterium having BChl f have not been found in the natural world. Previous reports have confirmed that artificial genetic engineering can be performed in the green sulfur bacterium *Chlorobaculum tepidum* having BChl c and the green sulfur bacterium *Chlorobaculum parvum* having BChl d (non-patent documents 3, 4). Therefore, studies relating to the biosynthetic pathway of the pigment have progressed and all synthase genes have been elucidated. By modifying the elucidated enzyme genes, chlorosomes constituted by various pigment molecular species have been produced in the living organism of variants. There are also variants greatly contributing to the elucidation of the structure of chlorosomes (non-patent document 5).

DOCUMENT LIST

Non-patent Documents non-patent document 1: H. Tamiaki (1996) Coord. Chem. Rev., 148: 183-197
non-patent document 2: V. I. Prokhorenko et al. (2002) J. Phys. Chem. B, 106: 5761-5768
non-patent document 3: N. U. Frigaard et al. (2003) Photosynth. Res., 78: 93-117
non-patent document 4: N. U. Frigaard (2004) Methods Mol. Biol., 274: 325-340
non-patent document 5: S. Ganapathy et al. (2009) Proc. Natl. Acad. Sci. USA., 106:8525-8530

SUMMARY OF THE INVENTION

Problems to be Solved by the Invention

Therefore, if pigment molecule, composition and the like can be controlled by genetic modification of green sulfur bacterium, a chlorosome having various functions can be formed. When the chlorosome is removed from the living organism and utilized, a great contribution can be made to the field of light energy capture and utilization thereof. In this sense, utilization of green sulfur bacterium targeting chlorosome can provide an realistic experiment system with a high utility value for nanoscience and nanotechnology.

On the other hand, there is no report on genetic engineering of bacteria having BChl e. Therefore, the biosynthetic pathway thereof still remains unknown. BChl e is different from BChl c and BChl d in that it has a formyl group at the C-7-position of the chlorin backbone, and characteristically shows a Qy peak on the shortest wavelength side among the three pigments since it has the side chain. Thus, if some green sulfur bacteria that synthesize BChl e can be genetically engineered, the biosynthetic pathway thereof can be elucidated, and various chlorosomes having absorption property in a wavelength region different from that of BChl c and BChl d can be created by genetic modification.

An object of the present invention is to provide a novel strain permitting genetic engineering of green sulfur bacteria that synthesize BChl e.

Means of Solving the Problems

To work on the development of a method of genetically engineering the green sulfur bacterium *Chlorobaculum limnaeum* (sometimes to be abbreviated as "*Cba. limnaeum*") having BChl e, the present inventors repeated passage culture of *Chlorobaculum limnaeum* strain 1549 for several years (about 8 years), and positively promoted spontaneous mutation. They isolated colonies and selected fast grown strains. They further performed a natural transformation method of the selected strains and the successfully isolated a strain permitting genetic engineering, which resulted in the completion of the present invention.

The present invention provides the following.

[1] An isolated green sulfur bacterium *Chlorobaculum limnaeum* strain RK-j-1 shown by accession number NITE BP-1202.
[2] An isolated transformant strain of *Chlorobaculum limnaeum* obtained by transforming the strain RK-j-1 of the aforementioned [1].
[3] The transformant strain of *Chlorobaculum limnaeum* of the aforementioned [2], wherein a bchU gene is disrupted.
[4] The transformant strain of *Chlorobaculum limnaeum* of the aforementioned [3], which is a *Chlorobaculum limnaeum* strain dbchU shown by accession number NITE BP-1203.
[5] A production method of bacteriochlorophyll f comprising a step of cultivating the transformant strain of *Chlorobaculum limnaeum* of the aforementioned [3] or [4].
[6] Bacteriochlorophyll f obtained by the production method of the aforementioned [5].
[7] Bacteriochlorophyll f produced by the *Chlorobaculum limnaeum* strain dbchU of the aforementioned [4].

[8] The bacteriochlorophyll f of the aforementioned [6] or [7], which is represented by the following formula:

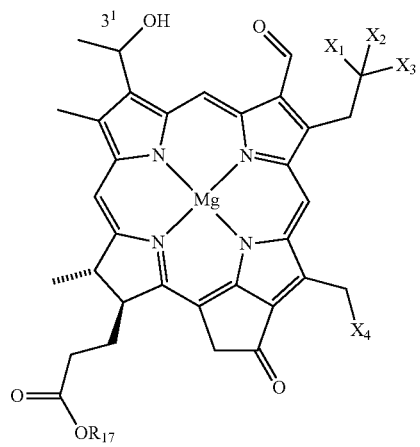

wherein $R_{17}$ is representatively a farnesyl group or optionally a phytyl group, a geranylgeranyl group, a dihydrogeranyl group or a tetrahydrogeranyl group, $X_1$, $X_2$, $X_3$ and $X_4$ are the same or different and each is a hydrogen atom or a methyl group, and $3^1$ is a steric isomer (R or S configuration) of a 1-hydroxyethyl group.

[9] Bacteriochlorophyll f represented by the following formula:

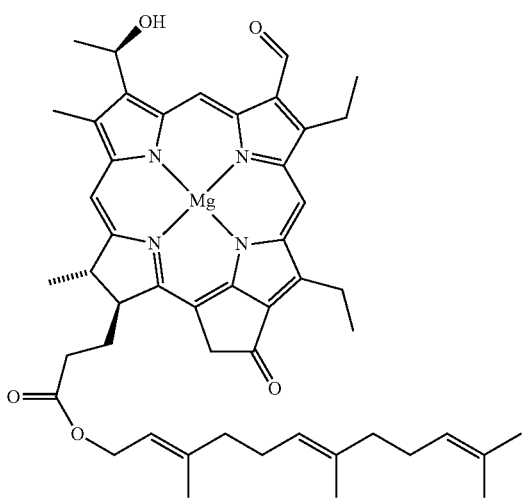

-continued

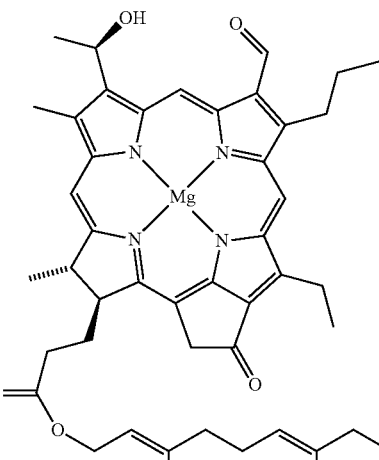

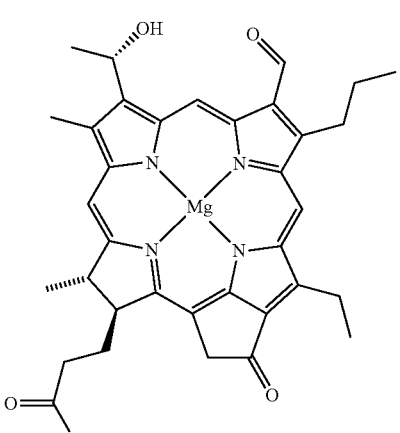

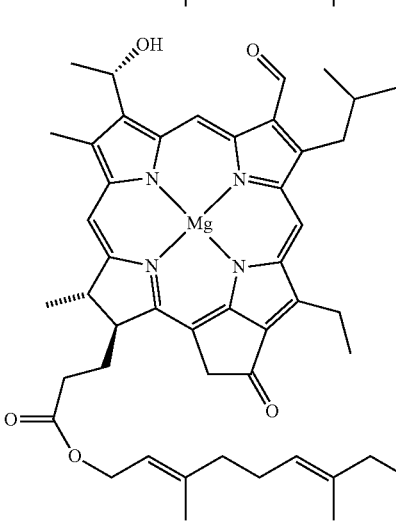

wherein 1 is R/C-8-position ethyl/C-12-position ethyl BChl f, 2 is R/C-8-position propyl/C-12-position ethyl BChl f, 3 is S/C-8-position propyl/C-12-position ethyl BChl f, and 4 is S/C-8-position isobutyl/C-12-position ethyl BChl f.

[10] A reconstituted chlorosome comprising the bacteriochlorophyll f of any one of the aforementioned [6]-[9] as a constituent component.

Effect of the Invention

According to the present invention, the green sulfur bacterium *Chlorobaculum limnaeum* strain RK-j-1 permitting transformation by gene recombination can be provided. Since transformation of green sulfur bacteria having BChl e has heretofore been difficult, the study of genetic engineering of *Chlorobaculum limnaeum* is expected to progress by utilizing strain RK-j-1 of the present invention. Specifically, the pigment molecule, composition and the like of the strain can be controlled by genetic modification. It is possible to form a chlorosome having various functions by utilizing strain RK-j-1. By removing the chlorosome from the living organism and utilizing same, a great contribution to the field of light energy capture and light energy utilization is expected.

According to the bchU gene disruptant of strain RK-j-1 of the present invention, a green sulfur bacterium having BChl f, which has not been found in the natural world to date, can be provided. The bchU gene disruptant can supply BChl f showing a Qy peak shifting toward shorter wavelength side than BChl e can be provided.

According to the present invention, moreover, novel BChl f can be provided, using which various chlorosomes are reconstituted outside the living organism, and application thereof to the field of light energy capture and light energy utilization is expected.

DESCRIPTION OF EMBODIMENTS

Figure 1:
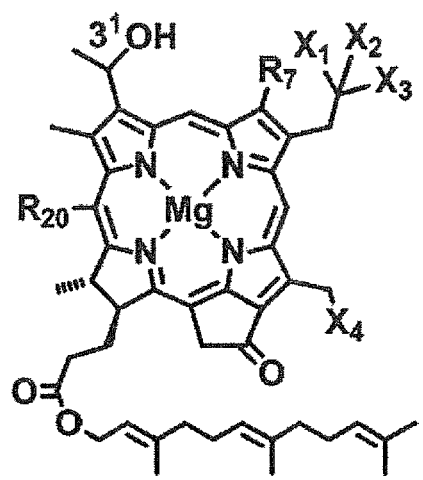
FIG. 1 shows molecular structures of the representative BChl c, BChl d, BChl e and BChl f.

The "green sulfur bacterium *Chlorobaculum limnaeum*", which is the target in the present invention, as a wild type strain has bacteriochlorophyll e as a pigment molecule, and has a chlorosome formed by self-aggregation of the pigment molecules. In the present invention, *Chlorobaculum limnaeum* strain 1549 preserved in Kurume University School of Medicine, Department of Medical Biochemistry, is used as a parent strain. *Chlorobaculum limnaeum* strain 1549 is also available from the researchers in the pertinent technical field.

The present invention provides the green sulfur bacterium *Chlorobaculum limnaeum* strain RK-j-1 (hereinafter sometimes to be abbreviated as "strain RK-j-1") permitting gene transformation, which is isolated from the passage culture of green sulfur bacterium *Chlorobaculum limnaeum* strain 1549.

Strain RK-j-1 was obtained by isolating clones, which became transformable after several years (about 8 years) of continuous culture of parent strain 1549 which was incapable of transformation. It is considered attributable to a natural mutation that occurred during the long-term continuous cultivation. 16S rDNA matches by not less than 99.99% with the base sequence of *Chlorobaculum limnaeum* registered in the Genebank (Accession No.: AJ299413, registered in old name, *Chlorobium phaeobacteroides* strain 1549). It is morphologically almost the same as parent strain 1549, and can grow photoautotrophically by anaerobic photosynthetic culture.

Strain RK-j-1 can be cultivated under conditions similar to those for general green sulfur bacterium. Preferable specific example of the culture conditions are as follows.

(1) Medium:

Green sulfur bacterium medium (NBRC Medium No. 855) CL medium (liquid medium): per 1 L, 20 mL of salts A (0.64 g $Na_2EDTA\ 2H_2O$, 10 g $MgSO_4\ 7H_2O$, 2.5 g $CaCl_2\ 2H_2O$, 20 g NaCl/1 L), 20 mL of salts B (25 g $CH_3COONH_4$, 20 g $NH_4Cl$, 115 g $Na_2S_2O_3\ 5H_2O$/1 L), 20 mL of CL/CP buffer (25 g $KH_2PO_4$, 115 g MOPS [3-{N-morpholino}propane sulfonic acid]/1 L), 1 mL of trace element solution (5.2 g 2Na EDTA, 0.19 g $CoCl_2\ 6H_2O$, 0.1 g $MnCl_2\ 4H_2O$, 1.5 g $FeCl_2\ 4H_2O$, 0.006 g $H_3BO_3$, 0.017 g $CuCl_2\ 2H_2O$, 0.188 g $Na_2MoO_4\ 2H_2O$, 0.025 g $NiCl_2\ 6H_2O$, 0.07 g $ZnCl_2$, 0.03 g $VOSO_4$, 0.002 g $Na_2WO_4\ 2H_2O$, 0.002 g $Na_2HSeO_3$/1 L), 50 μL of Resazurin (10 mg/mL), 20 μL of vitamin $B_{12}$ (1 mg/mL) are added, and the mixture is diluted with distilled water to 1 L in a measuring cylinder (measured up). After autoclaving at 121° C. for about 20 min, 50 mL of $Na_2S\ 9H_2O$/$NaHCO_3$ solution (0.6 g $Na_2S\ 9H_2O$, 2.0 g $NaHCO_3$/50 mL) after sterilization by filtration is added, and the pH is adjusted to 6.9-7.0.

CP plate (solid plating medium): per 1 L, 20 mL of salts A, 20 mL of salts B, 1 mL of trace element solution, 50 μL of 10 mg/mL Resazurin, 20 μL of vitamin $B_{12}$ and 0.36 g of L-cysteine are added, the pH is adjusted to 7.6 with 10 M NaOH, 15 g of agar (Bacto Agar™) is added, and the mixture is autoclaved at 121° C. for about 20 min, cooled to 50° C., dispensed to culture dish to allow for solidification, and moved to the anaerobic chamber (operation is performed within 60 min after autoclaving to prevent excess oxidation of L-cysteine).

(2) Culture Conditions

Cultivated in anaerobic chamber at 30° C. under obligately anaerobic conditions with pure nitrogen substitution.

(3) Long-term Preservation Conditions

Cryopreserved (−80° C. or below) in a medium containing 5% DMSO or 15% glycerol.

For the detail of the culture conditions, refer to Frigaad N U and Bryant D A, Appl. Environ. Microbiol., 67; 2538-2544 (2001) and Frigaad N U, Sakuragi Y and Bryant D A, Methods Mol. Biol., 274; 325-340 (2004).

*Chlorobaculum limnaeum* strain RK-j-1 was deposited on Jan. 12, 2012 (the date of original deposit) in the Incorporated Administrative Agency National Institute of Technology and Evaluation Patent Microorganisms Depositary (2-5-8 Kazusakamatari Kisarazu-shi, Chiba-ken, Japan) under reference number NITE AP-1202 (accession number NITE P-1202). Conversion of deposit of NITE P-1202 to a deposit under the Budapest Treaty was requested based on the Budapest Treaty, the request was accepted on Dec. 25, 2012 (date of conversion) and the strain is internationally deposited under accession number: NITE BP-1202.

Different from general *Chlorobaculum limnaeum* having bacteriochlorophyll e, strain RK-j-1 is a transformable strain. The present invention provides an isolated transformant strain of *Chlorobaculum limnaeum*, which is obtained by transforming strain RK-j-1.

Transformation can be performed by natural transformation. Natural transformation includes preparing cultured strain RK-j-1 in the logarithmic phase, recovering the cells by centrifugation, mixing with the above-mentioned CL medium and nucleic acid (DNA etc.) to be the introduction target, plating on a CP plate, incubating for 3-5 days, and spreading the grown cells on the CP plate to form colonies. In this case, to distinguish the transformed cells, it is desirable to simultaneously introduce an antibiotic resistance gene and cultivate the cells on a CP plate containing the antibiotic. The grown colonies are picked up, and the presence or absence of introduction of the object gene is confirmed by PCR and sequence analysis.

For the detail of the transformation method of green sulfur bacterium, refer to Environ. Microbiol., 67; 2538-2544 (2001), Methods Mol. Biol., 274; 325-340 (2004) and the like.

Figure 2:
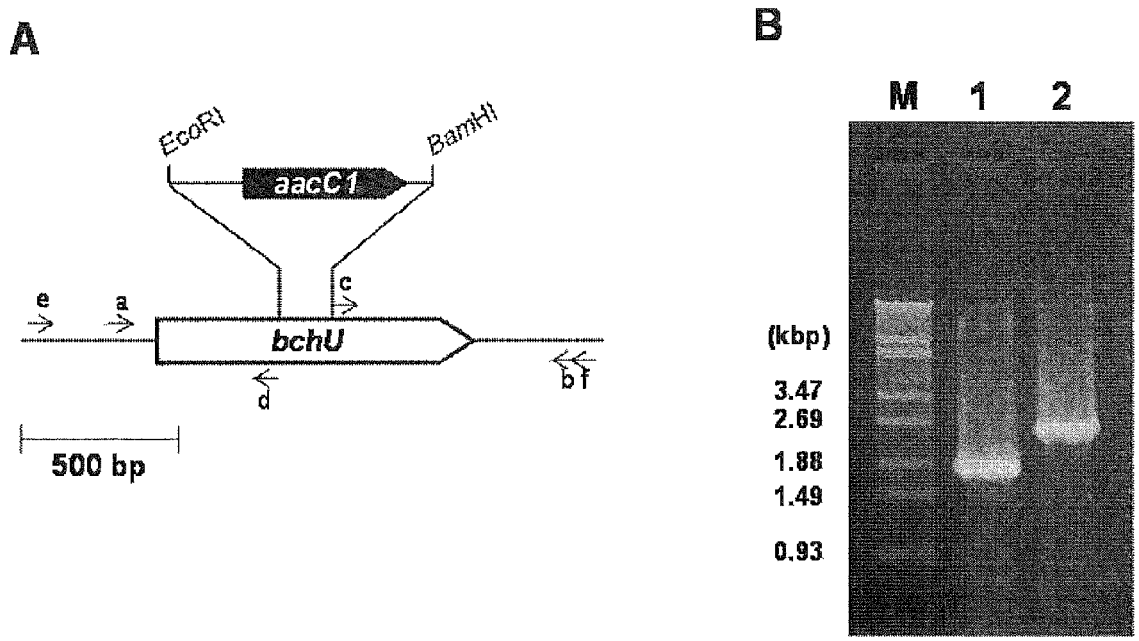
FIG. 2 shows production of a bchU gene disruptant of *Cba. limnaeum*. (A) is a schematic showing of the genome around bchU gene of *Cba. limnaeum*. The bchU disruptant was constituted to prevent expression of normal gene product by substituting a part of bchU gene with aacC1 gene (gentamicin (antibiotic) resistance gene). Arrows show bchU F1 (a), bchU R1 (b), bchU F2 (c), bchU R2 (d), bchU comf. F (e), and bchU comf. R (f) primers. (B) Confirmation of gene disruption by PCR. Using bchU comf. F and R primers, a region near bchU gene in the genome DNAs of wild type strain and bchU gene disruptant was amplified by PCR, and the product was confirmed by agarose gel electrophoresis. A band of 1.83 kbp DNA fragment was confirmed in the wild type strain (lane 1), and a band of 2.51 kbp was confirmed in the disruptant (lane 2). Lane M shows a DNA molecular weight size marker (size of each band is shown on the left side of lane M).

As one preferable embodiment of transformation, disruption of bchU gene can be mentioned. The bchU gene encodes an enzyme that methylates (methyltransferase) the 20-position of chlorin backbone by using S-adenosylmethionine (SAM) as a methyl group donor. The expression of bchU gene can be suppressed by using a targeting vector that targets the gene. Specifically, as shown in FIG. 2, a part of the bchU gene is replaced by a drug resistance gene (e.g., aacC1 gene: gentamicin resistance gene), whereby homologous recombination can be induced to prevent expression of a normal bchU gene product.

The thus-obtained bchU disruptant derived from *Chlorobaculum limnaeum* strain RK-j-1 lacks an enzyme that transfers methylation to the 20-position of the chlorin backbone, and therefore, produces bacteriochlorophyll f wherein the 20-position of bacteriochlorophyll e is demethylated (see FIG. 1).

The present invention provides a bchU disruptant derived from *Chlorobaculum limnaeum* strain RK-j-1. The disruptant was named *Chlorobaculum limnaeum* strain dbchU, deposited on Jan. 12, 2012 (the date of original deposit) in the Incorporated Administrative Agency National Institute of Technology and Evaluation Patent Microorganisms Depositary (2-5-8 Kazusakamatari Kisarazu-shi, Chiba-ken, Japan) under the reference number NITE AP-1203 (accession number NITE P-1203). Conversion of deposit of NITE P-1203 to a deposit under the Budapest Treaty was requested based on the Budapest Treaty, the request was accepted on Dec. 25, 2012 (date of conversion) and the strain is internationally deposited under accession number: NITE BP-1203.

Strain dbchU is morphologically almost the same as parent strain RK-j-1, and can grow under the culture conditions and preservation conditions similar to those for strain RK-j-1. Since strain dbchU has aacC1 gene, it can grow even in the presence of 50 μg/mL gentamicin.

As for bacteriochlorophyll f, its existence in the natural world is not known, and only a part of the structures of bacteriochlorophyll f have organically been synthesized (H. Tamiaki et al. (2011) Photosynth. Res., 107: 133-138). Bacteriochlorophyll f is provided by cultivating the bchU disruptant (strain dbchU) of the present invention. In addition, a production method of bacteriochlorophyll f, which includes a cultivation step of the bchU disruptant (strain dbchU), is also provided.

In the production method of bacteriochlorophyll f, the bchU disruptant (strain dbchU) is cultivated in a CL medium containing 50 μg/mL gentamicin, in the same manner as with the parent strain (RF-j-1).

The structure of the bacteriochlorophyll f produced by the bchU disruptant (strain dbchU) of the present invention is as follows.

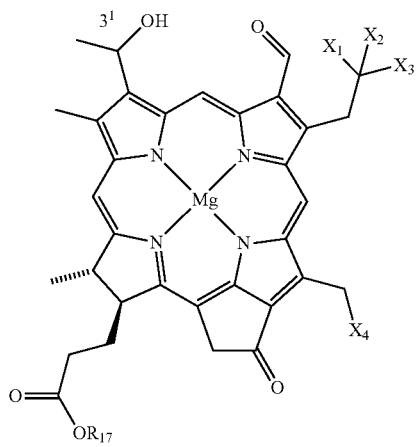

wherein $R_{17}$ is representatively a farnesyl group or optionally a phytyl group, a geranylgeranyl group, a dihydrogeranyl group or a tetrahydrogeranyl group, $X_1$, $X_2$, $X_3$ and $X_4$ are the same or different and each is a hydrogen atom or a methyl group, and $3^1$ is a steric isomer (R or S configuration) of a 1-hydroxyethyl group.

The structure of the aforementioned bacteriochlorophyll f wherein $R_{17}$ is a farnesyl group is as follows.

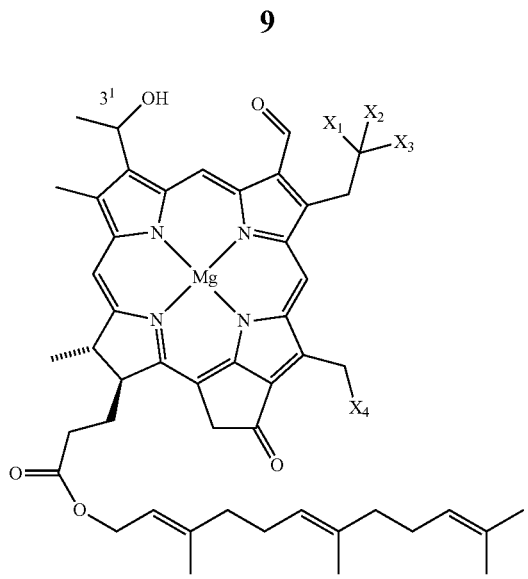

wherein

X$_1$, X$_2$, X$_3$ and X$_4$ are the same or different and each is a hydrogen atom or a methyl group, and 3$^1$ is a steric isomer (R or S configuration) of a 1-hydroxyethyl group.

Of the bacteriochlorophyll f represented by the above-mentioned formula, R/C-8-position ethyl/C-12-position methyl BChl f and S/C-8-position ethyl/C-12-position methyl BChl f can also be synthesized organic chemically according to a synthesis method known per se in the field of organic chemistry or the method described in previous reports (H. Tamiaki et al. (2011) Photosynth. Res., 107: 133-138).

Moreover, the present invention provides novel bacteriochlorophyll f represented by the following structural formula.

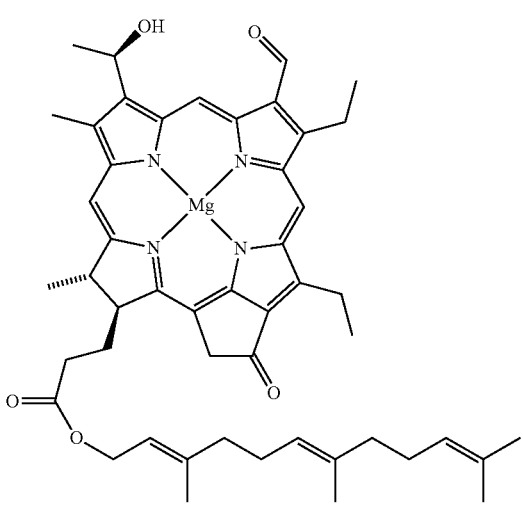

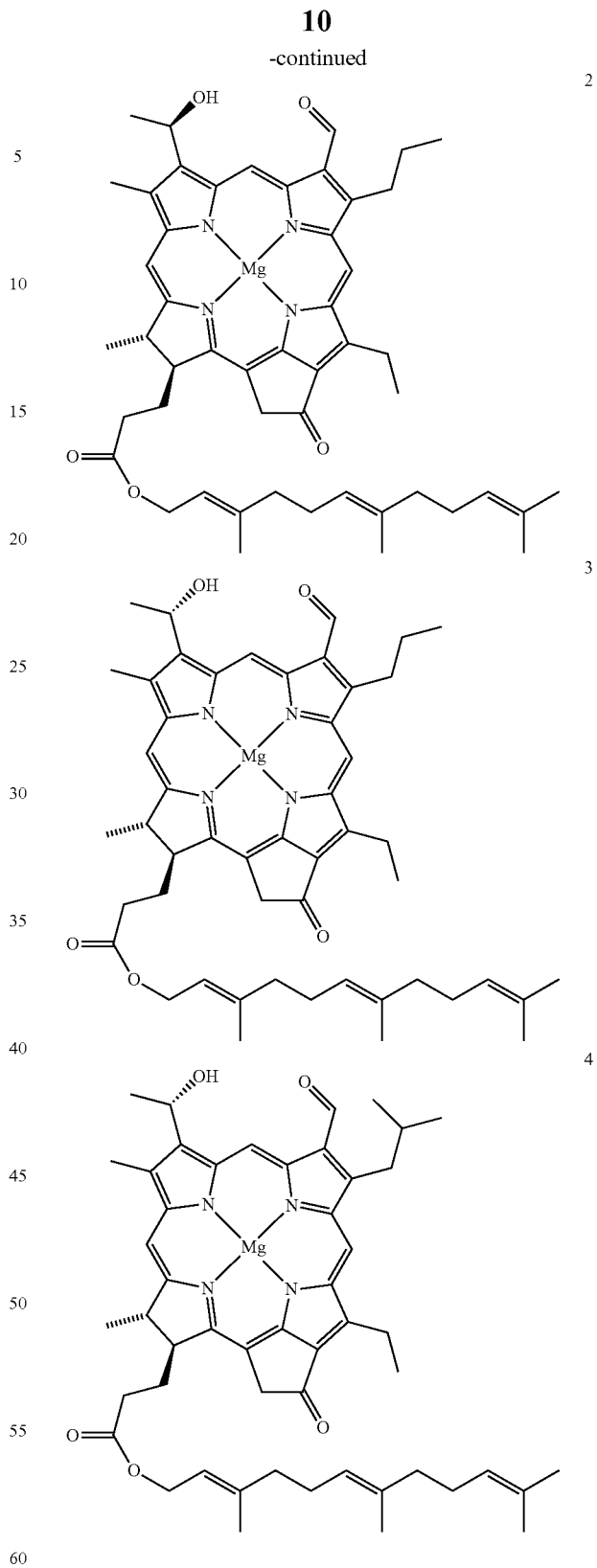

wherein 1 is R/C-8-position ethyl/C-12-position ethyl BChl f,
2 is R/C-8-position propyl/C-12-position ethyl BChl f,
3 is S/C-8-position propyl/C-12-position ethyl BChl f, and
4 is S/C-8-position isobutyl/C-12-position ethyl BChl f.

The structures of the novel bacteriochlorophyll f provided by the present invention are described with abbreviation:

R/C-8-position ethyl/C-12-position ethyl (R[E,E]) BChl f; R/C-8-position propyl/C-12-position ethyl (R[P,E]) BChl f; S/C-8-position propyl/C-12-position ethyl (S[P,E]) BChl f; S/C-8-position isobutyl/C-12-position ethyl (S[I, E]) BChl f.

Using the bacteriochlorophyll f of the present invention, chlorosome can be reconstituted in vitro, and the present invention provides a reconstituted chlorosome. Chlorosome can be reconstituted outside the living organism by self-aggregation capability of BChl c, d, e and f. These pigments are extracted from the living organism, and placed in a low polarity organic solvent, a water-organic solvent mixed solution or in water-soluble condition with a surfactant, whereby the pigments are self-accumulated to reconstruct a chlorosome.

EXAMPLES

The present invention is explained in more detail in the following by referring to Examples, to which the present invention is not limited in any way.

Example 1

Continuous Culture and Transformation of Strain 1549

*Chlorobaculum limnaeum* strain 1549 having BChl e (strain preserved in Kurume University School of Medicine, Department of Medical Biochemistry via Ritsumeikan University, Faculty of Pharmacy, Bioorganic chemical laboratory) was repeatedly passage cultured for several years (about 8 years) to positively promote spontaneous mutation. Culture was performed at 30° C. under light irradiation in a CL medium placed in a test tube having a screw cap. After reaching sufficient growth, the strain was placed in a dark place at room temperature. It was passaged in 3-6 month cycles, followed by growing on a CP plate to allow for colony formation, which was performed in one year cycles. The plate culture was performed in an anaerobic jar by using an $H_2/CO_2$ generation gas pack and the like.

The colonies were isolated and fast grown strains were selected. Some of the selected strains were subjected to natural transformation and strains permitting genetic engineering were selected. As a genetic modification region, enzyme gene bchU considered to modify a methyl group at the C-20-position of BChl e was selected. Whether replacement of the region with gentamicin resistance gene aacC1 occurs by homologous recombination was confirmed.

Two kinds of strains showing faster growth than other colonies were selected from the passage culture of *Chlorobaculum limnaeum* strain 1549 and named strain RK-j-1 and strain RK-j-2. The two strains were subjected to natural transformation. The majority of bchU cloned from *Chlorobaculum limnaeum* strain 1549 was replaced with aacC1 and the obtained plasmid was mixed with strain RK-j-1 or strain RK-j-2, spotted on a CP plate without medicament addition, and grown in an anaerobic jar at 30° C. for 3-7 days. The spot was scraped off, suspended in a CL liquid medium, and spread on a plate added with gentamicin (final concentration 50 μg/mL). After 7-14 days, the plate was confirmed. As a result, colony formation was confirmed only in the mixture of strain RK-j-1 and plasmid. The colony was cultured in a CL liquid medium added with gentamicin (final concentration 50 μg/mL), genome DNA was extracted and the neighboring genes including the bchU gene were amplified by a RCR method. The PCR product was subjected to agarose gel electrophoresis. As a result, a band of the size considered to show insertion of aacC1 into the bchU gene region was detected (FIG. 2). Then, the DNA sequence was confirmed by DNA sequencing. As a result, insertion of aacC1 into the bchU gene was confirmed. The strain derived from this colony was named bchU disruptant (strain dbchU).

Example 2

Extraction of Pigment Compound from BchU Disruptant

A pigment lacking a methyl group at the C-20-position of BChl e is called BChl f (FIG. 1), and shifting of Qy peak to the short wavelength side was confirmed in vitro (H. Tamiaki et al. (2011) Photosynth. Res., 107: 133-138).

Figure 3:
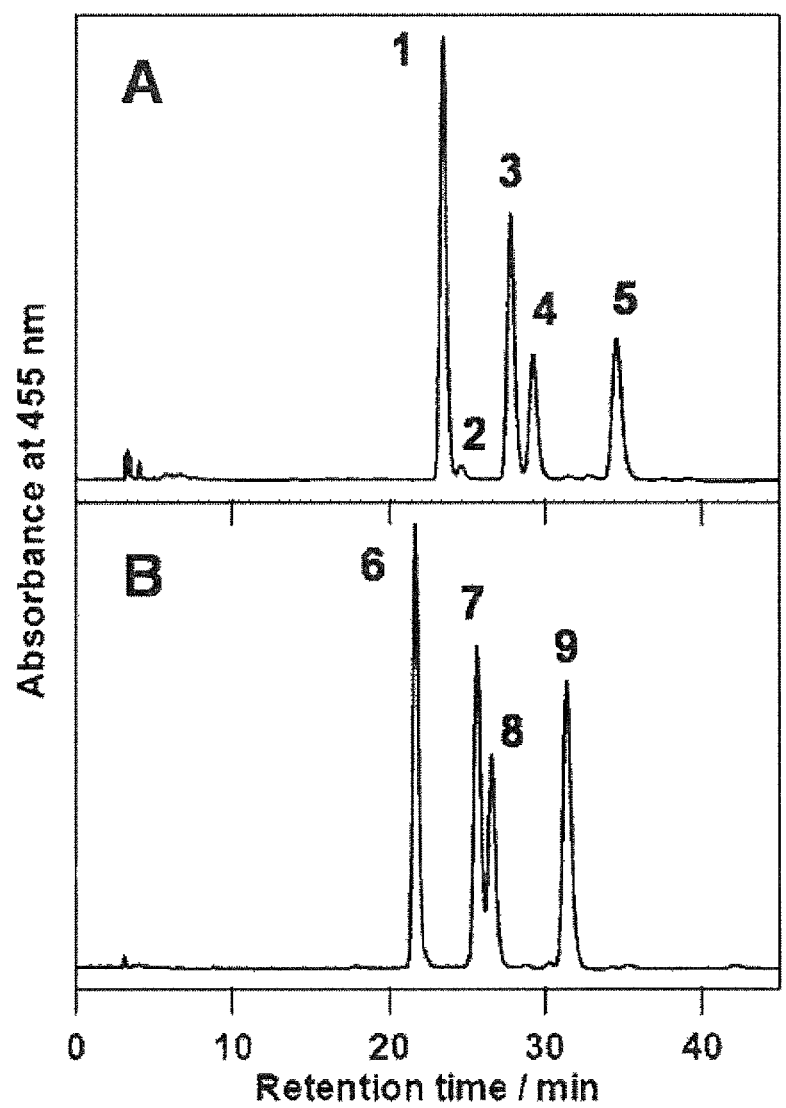
FIG. 3 shows the analysis results of the pigment composition of a bchU gene disruptant of *Cba. limnaeum*. Pigments were extracted from wild type strain (A) and bchU disruptant (B), and analyzed by LC-MS. In the wild type strain, a homolog of BChl e was detected, which was not found at all in the disruptant, and accumulation of BChl e instead of BChl f was clarified. peak 1, R/C-8-position ethyl/C-12-position ethyl (R[E,E]) BChl e (MW: 820.44 Da); peak 2, S/C-8-position ethyl/C-12-position ethyl (S[E,E]) BChl e; peak 3, R/C-8-position propyl/C-12-position ethyl (R[P,E]) BChl e (MW: 834.46 Da); peak 4, S/C-8-position propyl/C-12-position ethyl (S[P,E]) BChl e (MW: 834.46 Da); peak 5, S/C-8-position isobutyl/C-12-position ethyl (S[I,E]) BChl e (MW: 848.47 Da); peak 6, R/C-8-position ethyl/C-12-position ethyl (R[E,E]) BChl f (MW: 806.43 Da); peak 7, R/C-8-position propyl/C-12-position ethyl (R[P,E]) BChl f (MW: 820.44 Da); peak 8, S/C-8-position propyl/C-12-position ethyl (S[P,E]) BChl f (MW: 820.44 Da); peak 9, S/C-8-position isobutyl/C-12-position ethyl (S[I,E]) BChl f (MW: 834.46 Da). R and S show the absolute structures on the asymmetric carbon atom at the C-3-position of 1-hydroxyethyl group.

Pigments were extracted from the bchU disruptant according to a previous report (H. Tamiaki et al. (2011) Photosynth. Res., 107: 133-138), and compared with that of the wild type strain to confirm shifting of Qy peak to a short wavelength. Furthermore, pigment composition was analyzed by LC-MS. As a result, BChl e was not detected at all in the disruptant but, instead, accumulation of BChl f was found (FIG. 3).

BChl c, d and e are known to contain a homolog having a different side chain at the C-3-position, 8-position and C-12-position in the living organism. BChl f accumulated in the bchU disruptant was similarly present as a mixture of homologs in the living organism. The R/C-8-position ethyl/C-12-position methyl BChl f and S/C-8-position ethyl/C-12-position methyl BChl f are organically synthesized known pigments (H. Tamiaki et al. (2011) Photosynth. Res., 107: 133-138). These two kinds of BChl f are not present in the bchU disruptant, and R[E,E]BChl f, R[P,E]BChl f, S[P,E]BChl f and S[P,E]BChl f were detected. These are all novel pigment compounds.

Transformation by gene recombination could be performed by using strain RK-j-1 isolated after passage culture of *Chlorobaculum limnaeum* strain 1549 for many years. To demonstrate that transformation is possible, bchU gene was destroyed. The bchU disruptant lost its inherent BchU enzyme function, as a result of which BChl f was accumulated as a mixture of homologs. They were all novel pigment compounds and identified as R[E, E]BChl f, R[P, E]BChl f, S[P, E]BChl f and S[I, E]BChl f.

The green sulfur bacterium *Chlorobaculum limnaeum* strain RK-j-1 of the present invention permits transformation by gene recombination, and the pigment molecule, composition and the like of the strain can be controlled by genetic modification. It is possible to form a chlorosome having various functions by using strain RK-j-1. By removing the chlorosome from the living organism and utilizing same, a great contribution to the field of light energy capture and light energy utilization is expected. From such aspect, utilization of green sulfur bacterium targeting chlorosome can provide a realistic experiment system with a high utility value for nanoscience and nanotechnology.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

This application is based on patent application No. 2012-028919 (filing date: Feb. 13, 2012) filed in Japan, the contents of which are encompassed in full herein.

The invention claimed is:

1. An isolated green sulfur bacterium *Chlorobaculum limnaeum* strain RK-j-1 deposited at National Institute of Technology and Evaluation Patent Microorganisms Depositary (NPMD) as accession number NITE BP-1202.

2. The strain RK-j-1 of claim 1 comprising a genome comprising an exogenous nucleic acid sequence.

3. The strain RK-j-1 of claim 2, wherein a bchU gene is disrupted by the exogenous nucleic acid sequence.

4. The strain RK-j-1 of claim 3, which is a *Chlorobaculum limnaeum* strain dbchU deposited at National Institute of Technology and Evaluation Patent Microorganisms Depositary (NPMD) as accession number NITE BP-1203.

5. A method of producing bacteriochlorophyll f comprising:
   cultivating the strain RK-j-1 of claim 3, and
   isolating the bacteriochlorophyll f.

6. An isolated bacteriochlorophyll f obtained by the method of claim 5.

7. The bacteriochlorophyll f of claim 6, which has the following formula:

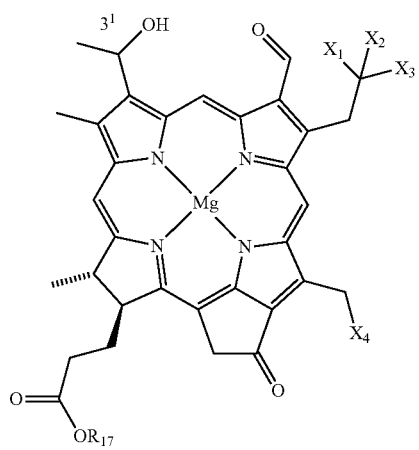

wherein
   $R_{17}$ is a farnesyl group, a phytyl group, a geranylgeranyl group, a dihydrogeranyl group or a tetrahydrogeranyl group,
   $X_1$, $X_2$, $X_3$ and $X_4$ are the same or different and each is a hydrogen atom or a methyl group, and
   $3^1$ is a steric isomer (R or S configuration) of a 1-hydroxyethyl group.

8. An isolated bacteriochlorophyll f having one of the following formulas:

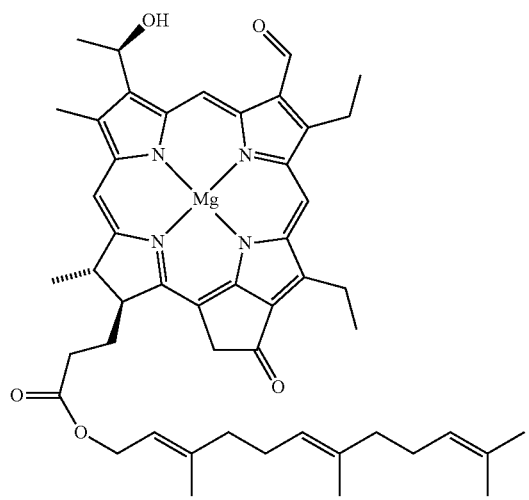

1

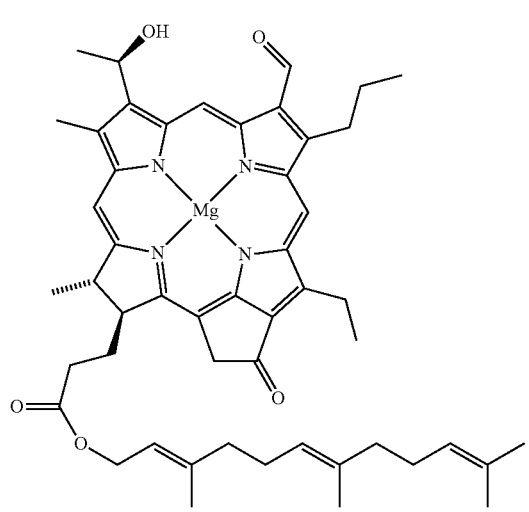

2

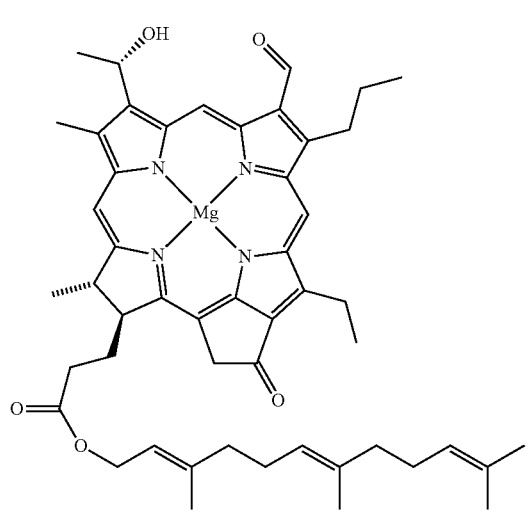

3

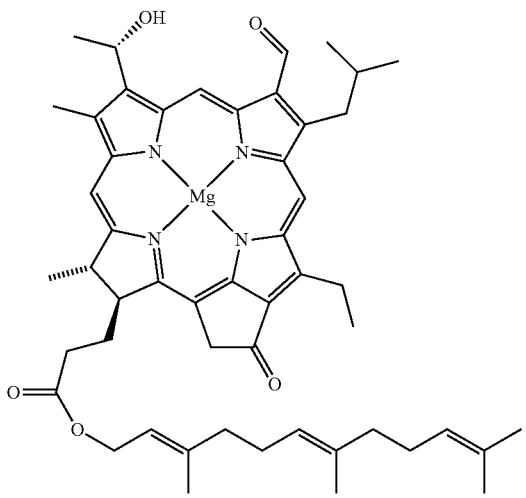

wherein 1 is R/C-8-position ethyl/C-12-position ethyl BChl f, 2 is R/C-8-position propyl/C-12-position ethyl BChl f, 3 is S/C-8-position propyl/C-12-position ethyl BChl f, and 4 is S/C-8-position isobutyl/C-12-position ethyl BChl f.

9. A reconstituted chlorosome comprising the bacteriochlorophyll f of claim 6 as a constituent component.

10. A method of producing bacteriochlorophyll f comprising:

cultivating the *Chlorobaculum limnaeum* strain dbchU of claim 4, and isolating the bacteriochlorophyll f.

11. An isolated bacteriochlorophyll f obtained by the method of claim 10.

12. The bacteriochlorophyll f of claim 11, which has the following formula:

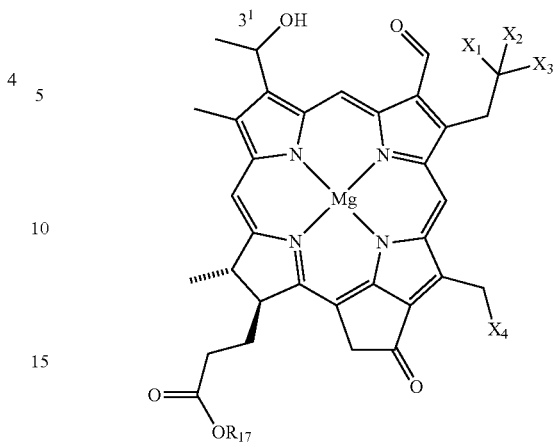

wherein $R_{17}$ is a farnesyl group, a phytyl group, a geranylgeranyl group, a dihydrogeranyl group or a tetrahydrogeranyl group, $X_1, X_2, X_3$ and $X_4$ are the same or different and each is a hydrogen atom or a methyl group, and $3^1$ is a steric isomer (R or S configuration) of a 1-hydroxyethyl group.

13. A reconstituted chlorosome comprising the bacteriochlorophyll f of claim 7 as a constituent component.

14. A reconstituted chlorosome comprising the bacteriochlorophyll f of claim 8 as a constituent component.

15. A reconstituted chlorosome comprising the bacteriochlorophyll f of claim 11 as a constituent component.

16. A reconstituted chlorosome comprising the bacteriochlorophyll f of claim 12 as a constituent component.

17. A method of preparing the strain RK-j-1 of claim 2, comprising:

(1) introducing into cells of the strain RK-j-1 a nucleic acid that comprises a nucleic acid sequence homologous to a genome sequence of the strain RK-j-1 and an exogenous gene, thereby preparing a transformed cell distinguishable from non-transformed cell, (2) culturing the cells of the strain RK-j-1 obtained in step (1) to cause the insertion of the nucleic acid into the genome by homologous recombination, and (3) selecting the transformed cell using the expression of the exogenous gene as an index.

18. The method of claim 17, wherein the exogenous gene is a drug resistance gene.

19. The strain RK-j-1 of claim 2, wherein the exogenous nucleic acid sequence comprises a drug resistance gene.

* * * * *